United States Patent [19]
Bienkowski

[11] Patent Number: 6,031,089
[45] Date of Patent: Feb. 29, 2000

[54] SEQUENCES OF P56, PROTEINS WHICH AFFECT K-ATP CHANNELS

[75] Inventor: Michael J. Bienkowski, Portage, Mich.

[73] Assignee: Pharmacia & Upjohn Company, Kalamazoo, Mich.

[21] Appl. No.: 08/993,260

[22] Filed: Dec. 18, 1997

Related U.S. Application Data

[60] Provisional application No. 60/034,560, Dec. 30, 1996.

[51] Int. Cl.[7] .......................... C07H 21/04; C12N 15/12; C12N 15/63
[52] U.S. Cl. ......................... 536/23.5; 530/350; 530/300; 536/23.1; 435/320.1; 435/69.1; 435/325; 435/252.3; 435/235.1
[58] Field of Search ........................ 536/23.5; 530/350, 530/300; 435/7.1, 325, 69.1, 353, 250.3, 254.1, 255.1, 320.1, 235.1

[56] References Cited

U.S. PATENT DOCUMENTS 5,525,724  6/1996  Gadwood et al. .......................... 552/8

FOREIGN PATENT DOCUMENTS

| WO 94/19464 | 9/1994 | WIPO ............................. C12N 15/12 |
| WO 94/194645 | 9/1994 | WIPO . |
| WO 96/16088 | 5/1996 | WIPO . |

OTHER PUBLICATIONS

George et al., Current Methods in Sequence Comparison Comparison and Analysis, selected methods and applications. Edited by David H. Schlesinger, Alan R. Liss, Inc., New York pp. 124–129.
Tokuymam et al, Rat Inwardly Rectifying Potassium Channel Kir6.2, Biochemical and Biophysical research Communications, vol. 220, pp. 532–538.
Inagaki et al, Cloning and Functional Characterization of a Novel ATP–sensitive Potassium Channel Ubiquitously Expressed in Rat Tissues, Including Pancreatic Islets, Pituitary, Skeletal Muscle and Heart, The Journal of Biological Chemistry, vol. 270, pp. 5691–5694.
Noma, A., *Nature*, 305, pp. 147–148 (1983).
Spruce, A. E., et al., *Nature*, 316, pp. 736–738 (1985).
Standen, N. B., et al., *Science*, 245, pp. 177–180 (1989).
Cook, D. L., et al., *Nature*, 311, pp. 271–273 (1984).
Sturgess, N. C., et al., *Lancet*, 2, pp. 474–475 (1985).
Rorsman, P., et al., *Pflugers Arch.*, 405, pp. 305–309 (1985).
Ashcroft, S. J. H., et al., *Cell Signal*, pp. 197–214 (1990).
Trube, G., et al., *Pflugers Arch*, 407, pp. 493–499 (1986).
Escande, D., et al., *Trends Pharmacol. Sci.*, pp. 269–271 (1992).
*Drug Dev. Res.*, 28, pp. 95–127 (1993).
Atwal, D. S., *Drug Dev. Res.*, 33, pp. 250–262 (1994).
Edwards, G., et al., *Ann. Rev. Pharmacol. Toxicol.*, 33, pp. 597–637 (1993).
de Weille, J. R., *Cardiovascular Res.*, 26, pp. 1017–1020 (1992).
Atwal, D. S., *Medicinal Research Rev.*, 12, pp. 569–591 (1992).
Robertson, D. W., et al., *J. Med. Chem.*, 33, pp. 1530–1541 (1990).
Inagaki, N., et al., *J. Biol. Chem.*, 270, pp. 5691–5694 (1995).
Aguilar–Bryan, L., et al., *Science*, 268, pp. 423–426 (1995).
Ho, K., et al., *Nature*, 362, pp. 31–38 (1993).
Dascal, N., et al., *Proc. Natl. Acad. Sci. USA*, 90, pp. 10235–10239 (1993).
Inagaki, N., et al., *Science*, 270, pp. 1166–170 (1995).
Tokuyama, Y., et al., *Biochem. Biophys. Res. Comm.*, 220, pp. 532–538 (1996).
Kramer. W., et al., *FEBS Let.*, 229, pp. 355–359 (1988).
Bernardi, H., et al., *Proc. Natl. Acad. Sci. USA*, 85, pp. 9816–9820 (1988).
Benardi, H., et al., *Biochemistry*, 31, pp. 6328–6332 (1992).
Aguilar–Bryan, L., et al., *J. Biol. Chem.*, 265, pp. 8218–8224 (1990).
Nelson, D. A., et al., *J. Biol. Chem.*, 267, pp. 14928–14933 (1992).
Bernardi, H., et al., *Proc. Natl. Acad. Sci. USA*, 90, pp. 1340–1344 (1993).
Schwanstecher, M., et al., *J. Biol. Chem.*, 269, pp. 17768–17771 (1994).
Schwanster, M., et al., *J. Neurochem.*, pp. 698–708 (1994).
Inagaki, N., et al., *Neuron*, 16, pp. 1011–1017 (1996).
Chutkow, W. A., et al., *Diabetes*, 45, pp. 1439–1445 (1996).
Isomoto, S., et al., *J. Biol. Chem.*, 271, pp. 24321–24324 (1996).
Dubray, C., et al., *FASEB Journal*, 10, p. A137 XP002064581 (1996).

*Primary Examiner*—Elizabeth Kemmerer
*Assistant Examiner*—Nirmal S. Basi
*Attorney, Agent, or Firm*—Thomas A Wootton

[57] ABSTRACT

This invention describes the full length sequence of human p56 protein (p56-1), a related homolog (p56-2) and the nucleic acids that code for these proteins. The sequences are provided in Charts 1, 2, 3, and 4 and the sequence listings of the application.

5 Claims, No Drawings

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 505 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:1:

```
Met Gly Arg Val Val Ala Glu Leu Val Ser Ser Leu Leu Gly Leu Trp
 1               5                  10                  15

Leu Leu Leu Cys Ser Cys Gly Cys Pro Glu Gly Ala Glu Leu Arg Ala
            20                  25                  30

Pro Pro Asp Lys Ile Ala Ile Gly Ala Gly Ile Gly Gly Thr Ser
            35                  40                  45

Ala Ala Tyr Tyr Leu Arg Gln Lys Phe Gly Lys Asp Val Lys Ile Asp
 50                  55                  60

Leu Phe Glu Arg Glu Glu Val Gly Gly Arg Leu Ala Thr Met Met Val
 65                  70                  75                  80

Gln Gly Gln Glu Tyr Glu Ala Gly Gly Ser Val Ile His Pro Leu Asn
                    85                  90                  95

Leu His Met Lys Arg Phe Val Lys Asp Leu Gly Leu Ser Ala Val Gln
                100                 105                 110

Ala Ser Gly Gly Leu Leu Gly Ile Tyr Asn Gly Glu Thr Leu Val Phe
            115                 120                 125

Glu Glu Ser Asn Trp Phe Ile Ile Asn Val Ile Lys Leu Val Trp Arg
            130                 135                 140

Tyr Gly Phe Gln Ser Leu Arg Met His Met Trp Val Glu Asp Val Leu
145                 150                 155                 160

Asp Lys Phe Met Arg Ile Tyr Arg Tyr Gln Ser His Asp Tyr Ala Phe
                    165                 170                 175

Ser Ser Val Glu Lys Leu Leu His Ala Leu Gly Gly Asp Asp Phe Leu
                180                 185                 190

Gly Met Leu Asn Arg Thr Leu Leu Glu Thr Leu Gln Lys Ala Gly Phe
            195                 200                 205
```

```
Ser Glu Lys Phe Leu Asn Glu Met Ile Ala Pro Val Met Arg Val Asn
    210                 215                 220

Tyr Gly Gln Ser Thr Asp Ile Asn Ala Phe Val Gly Ala Val Ser Leu
225                 230                 235                 240

Ser Cys Ser Asp Ser Gly Leu Trp Ala Val Glu Gly Asn Lys Leu
                245                 250                 255

Val Cys Ser Gly Leu Leu Gln Ala Ser Lys Ser Asn Leu Ile Ser Gly
                260                 265                 270

Ser Val Met Tyr Ile Glu Glu Lys Thr Lys Thr Lys Tyr Thr Gly Asn
            275                 280                 285

Pro Thr Lys Met Tyr Glu Val Val Tyr Gln Ile Gly Thr Glu Thr Arg
        290                 295                 300

Ser Asp Phe Tyr Asp Ile Val Leu Val Ala Thr Pro Leu Asn Arg Lys
305                 310                 315                 320

Met Ser Asn Ile Thr Phe Leu Asn Phe Asp Pro Pro Ile Glu Glu Phe
                325                 330                 335

His Gln Tyr Tyr Gln His Ile Val Thr Thr Leu Val Lys Gly Glu Leu
                340                 345                 350

Asn Thr Ser Ile Phe Ser Ser Arg Pro Ile Asp Lys Phe Gly Leu Asn
                355                 360                 365

Thr Val Leu Thr Thr Asp Asn Ser Asp Leu Phe Ile Asn Ser Ile Gly
370                 375                 380

Ile Val Pro Ser Val Arg Glu Lys Glu Asp Pro Glu Pro Ser Thr Asp
385                 390                 395                 400

Gly Thr Tyr Val Trp Lys Ile Phe Ser Gln Glu Thr Leu Thr Lys Ala
                405                 410                 415

Gln Ile Leu Lys Leu Phe Leu Ser Tyr Asp Tyr Ala Val Lys Lys Pro
                420                 425                 430

Trp Leu Ala Tyr Pro His Tyr Lys Pro Pro Glu Lys Cys Pro Ser Ile
            435                 440                 445

Ile Leu His Asp Arg Leu Tyr Tyr Leu Asn Gly Ile Glu Cys Ala Ala
        450                 455                 460

Ser Ala Met Glu Met Ser Ala Ile Ala Ala His Asn Ala Ala Leu Leu
465                 470                 475                 480

Ala Tyr His Arg Trp Asn Gly His Thr Asp Met Ile Asp Gln Asp Gly
                485                 490                 495

Leu Tyr Glu Lys Leu Lys Thr Glu Leu
                500                 505

(2) INFORMATION FOR SEQ ID NO:2:

(i) SEQUENCE CHARACTERISTICS:
        (A) LENGTH: 1724 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

CGCTCGGAAT TCGGCTCGAG TGCAGAGCTT GTGGAGGCCA TGGGGCGCGT CGTCGCGGAG      60

CTCGTCTCCT CGCTGCTGGG GTTGTGGCTG TTGCTGTGCA GCTGCGGATG CCCCGAGGGC     120
```

```
GCCGAGCTGC GTGCTCCGCC AGATAAAATC GCGATTATTG GAGCCGGAAT TGGTGGCACT      180

TCAGCAGCCT ATTACCTGCG GCAGAAATTT GGGAAAGATG TGAAGATAGA CCTGTTTGAA      240

AGAGAAGAGG TCGGGGGCCG CCTGGCTACC ATGATGGTGC AGGGGCAAGA ATACGAGGCA      300

GGAGGTTCTG TCATCCATCC TTTAAATCTG CACATGAAAC GTTTTGTCAA AGACCTGGGT      360

CTCTCTGCTG TTCAGGCCTC TGGTGGCCTA CTGGGGATAT ATAATGGAGA GACTCTGGTA      420

TTTGAGGAGA GCAACTGGTT CATAATTAAC GTGATTAAAT TAGTTTGGCG CTATGGATTT      480

CAATCCCTCC GTATGCACAT GTGGGTAGAG GACGTGTTAG ACAAGTTCAT GAGGATCTAC      540

CGCTACCAGT CTCATGACTA TGCCTTCAGT AGTGTCGAAA AATTACTTCA TGCTCTAGGA      600

GGAGATGACT TCCTTGGAAT GCTTAATCGA ACACTTCTTG AAACCTTGCA AAAGGCCGGC      660

TTTTCTGAGA AGTTCCTCAA TGAAATGATT GCTCCTGTTA TGAGGGTCAA TTATGGCCAA      720

AGCACGGACA TCAATGCCTT TGTGGGGGCG GTGTCACTGT CCTGTTCTGA TTCTGGCCTT      780

TGGGCAGTAG AAGGTGGCAA TAAACTTGTT TGCTCAGGGC TTCTGCAGGC ATCCAAAAGC      840

AATCTTATAT CTGGCTCAGT AATGTACATC GAGGAGAAAA CAAAGACCAA GTACACAGGA      900

AATCCAACAA AGATGTATGA AGTGGTCTAC CAAATTGGAA CTGAGACTCG TTCAGACTTC      960

TATGACATCG TCTTGGTGGC CACTCCGTTG AATCGAAAAA TGTCGAATAT TACTTTTCTC     1020

AACTTTGATC CTCCAATTGA GGAATTCCAT CAATATTATC AACATATAGT GACAACTTTA     1080

GTTAAGGGGG AATTGAATAC ATCTATCTTT AGCTCTAGAC CCATAGATAA ATTTGGCCTT     1140

AATACAGTTT TAACCACTGA TAATTCAGAT TTGTTCATTA ACAGTATTGG GATTGTGCCC     1200

TCTGTGAGAG AAAAGGAAGA TCCTGAGCCA TCAACAGATG GAACATATGT TTGGAAGATC     1260

TTTTCCCAAG AAACTCTTAC TAAAGCACAA ATTTTAAAGC TCTTTCTGTC CTATGATTAT     1320

GCTGTGAAGA AGCCATGGCT TGCATATCCT CACTATAAGC CCCCGGAGAA ATGCCCCTCT     1380

ATCATTCTCC ATGATCGACT TTATTACCTC AATGGCATAG AGTGTGCAGC AAGTGCCATG     1440

GAGATGAGTG CCATTGCAGC CCACAACGCT GCACTCCTTG CCTATCACCG CTGGAACGGG     1500

CACACAGACA TGATTGATCA GGATGGCTTA TATGAGAAAC TTAAAACTGA ACTATGAAGT     1560

GACACACTCC TTTTTCCCCT CCTAGTTCCA AATGACTATC AGTGGCAAAA AGAACAAAA      1620

TCTGAGCAGA GATGATTTTG AACCAGATAT TTTGCCATTA TCATTGTTTA ATAAAAGTAA     1680

TCCCTGCTGG TCATAGGAAA AAAAAAAAAA AAAAAAAAA AAAA                      1724
```

(2) INFORMATION FOR SEQ ID NO:3:

(i) SEQUENCE CHARACTERISTICS:
        (A) LENGTH: 494 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:3:

```
Met Ala Arg Ala Ala Pro Leu Leu Ala Ala Leu Thr Ala Leu Leu Ala
1               5                  10                  15

Ala Ala Ala Ala Gly Gly Asp Ala Pro Pro Gly Lys Ile Ala Val Val
            20                  25                  30
```

-continued

```
Gly Ala Gly Ile Gly Ser Ala Val Ala His Phe Leu Gln Gln His
         35                  40                  45

Phe Gly Pro Arg Val Gln Ile Asp Val Tyr Glu Lys Gly Thr Val Gly
 50                  55                  60

Gly Arg Leu Ala Thr Ile Ser Val Asn Lys Gln His Tyr Glu Ser Gly
 65                  70                  75                  80

Ala Ala Ser Phe His Ser Leu Ser Leu His Met Gln Asp Phe Val Lys
                 85                  90                  95

Leu Leu Gly Leu Arg His Arg Arg Glu Val Val Gly Arg Ser Ala Ile
                100                 105                 110

Phe Gly Gly Glu His Phe Met Leu Glu Glu Thr Asp Trp Tyr Leu Leu
            115                 120                 125

Asn Leu Phe Arg Leu Trp Trp His Tyr Gly Ile Ser Phe Leu Arg Leu
        130                 135                 140

Gln Met Trp Val Glu Glu Val Met Glu Lys Phe Met Arg Ile Tyr Lys
145                 150                 155                 160

Tyr Gln Ala His Gly Tyr Ala Phe Ser Gly Val Glu Glu Leu Leu Tyr
                165                 170                 175

Ser Leu Gly Glu Ser Thr Phe Val Asn Met Thr Gln His Ser Val Ala
            180                 185                 190

Glu Ser Leu Leu Gln Val Gly Val Thr Gln Arg Phe Ile Asp Asp Val
        195                 200                 205

Val Ser Ala Val Leu Arg Ala Ser Tyr Gly Gln Ser Ala Ala Met Pro
210                 215                 220

Ala Phe Ala Gly Ala Met Ser Leu Ala Gly Ala Gln Gly Ser Leu Trp
225                 230                 235                 240

Ser Val Glu Gly Gly Asn Lys Leu Val Cys Ser Gly Leu Leu Lys Leu
                245                 250                 255

Thr Lys Ala Asn Val Ile His Ala Thr Val Thr Ser Val Thr Leu His
            260                 265                 270

Ser Thr Glu Gly Lys Ala Leu Tyr Gln Val Ala Tyr Glu Asn Glu Val
        275                 280                 285

Gly Asn Ser Ser Asp Phe Tyr Asp Ile Val Val Ile Ala Thr Pro Leu
290                 295                 300

His Leu Asp Asn Ser Ser Asn Leu Thr Phe Ala Gly Phe His Pro
305                 310                 315                 320

Pro Ile Asp Asp Val Gln Gly Ser Phe Gln Pro Thr Val Val Ser Leu
                325                 330                 335

Val His Gly Tyr Leu Asn Ser Ser Tyr Phe Gly Phe Pro Asp Pro Lys
            340                 345                 350

Leu Phe Pro Phe Ala Asn Ile Leu Thr Thr Asp Phe Pro Ser Phe Phe
        355                 360                 365

Cys Thr Leu Asp Asn Ile Cys Pro Val Asn Ile Ser Ala Ser Phe Arg
370                 375                 380

Arg Lys Gln Pro Gln Glu Ala Ala Val Trp Arg Val Gln Ser Pro Lys
385                 390                 395                 400

Pro Leu Phe Arg Thr Gln Leu Lys Thr Leu Phe Arg Ser Tyr Tyr Ser
                405                 410                 415

Val Gln Thr Ala Glu Trp Gln Ala His Pro Leu Tyr Gly Ser Arg Pro
            420                 425                 430

Thr Leu Pro Arg Phe Ala Leu His Asp Gln Leu Phe Tyr Leu Asn Ala
        435                 440                 445

Leu Glu Trp Ala Ala Ser Ser Val Glu Val Met Ala Val Ala Ala Lys
```

```
            450              455              460
Asn Val Ala Leu Leu Ala Tyr Asn Arg Trp Tyr Gln Asp Leu Asp Lys
465              470              475              480

Ile Asp Gln Lys Asp Leu Met His Lys Val Lys Thr Glu Leu
                485              490
```

(2) INFORMATION FOR SEQ ID NO:4:

(i) SEQUENCE CHARACTERISTICS:
        (A) LENGTH: 2567 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

```
CCTGAATCCG GCGTGCTGCC CGCTCGCCGC CCGCCATGGC CCGCGCAGCC CCGCTGCTCG      60
CCGCGTTGAC CGCGCTCCTC GCCGCCGCCG CTGCTGGCGG AGATGCCCCG CCGGGCAAAA     120
TCGCGGTGGT TGGGGCTGGG ATTGGGGGCT CTGCTGTGGC CCATTTTCTC CAGCAGCACT     180
TTGGACCTCG GGTGCAGATC GACGTGTACG AGAAGGGAAC CGTGGGTGGC CGCTTGGCCA     240
CCATCTCAGT CAACAAGCAG CACTATGAGA GCGGGGCTGC CTCCTTCCAC TCCCTGAGCC     300
TGCACATGCA GGACTTCGTC AAGCTGCTGG GGCTGAGGCA CCGGCGCGAG GTGGTGGGCA     360
GGAGCGCCAT CTTCGGCGGG GAGCACTTCA TGCTGGAGGA GACTGACTGG TACCTGCTGA     420
ACCTCTTCCG CCTCTGGTGG CACTATGGCA TCAGCTTCCT GAGGCTGCAG ATGTGGGTGG     480
AGGAGGTCAT GGAGAAGTTC ATGAGGATCT ATAAGTACCA GGCCCACGGC TATGCCTTCT     540
CGGGTGTGGA GGAGCTGCTC TACTCACTGG GGGAGTCCAC CTTTGTTAAC ATGACCCAGC     600
ACTCTGTGGC TGAGTCCCTG CTGCAGGTGG GCGTCACGCA GCGCTTTATT GATGATGTCG     660
TTTCTGCTGT CCTGCGGGCC AGCTATGGCC AGTCAGCAGC GATGCCCGCC TTTGCAGGAG     720
CCATGTCACT AGCCGGGGCC CAAGGCAGCC TGTGGTCTGT GGAAGGAGGC AATAAGCTGG     780
TTTGTTCCGG TTTGCTGAAG CTCACCAAGG CCAATGTGAT CCATGCCACA GTGACCTCTG     840
TGACCCTGCA CAGCACAGAG GGGAAAGCCC TGTACCAGGT GGCGTATGAG AATGAGGTAG     900
GCAACAGCTC TGACTTCTAT GACATCGTGG TCATCGCCAC CCCCCTGCAC CTGGACAACA     960
GCAGCAGCAA CTTAACCTTT GCAGGCTTCC ACCCGCCCAT TGATGACGTG CAGGGCTCTT    1020
TCCAGCCCAC CGTCGTCTCC TTGGTCCACG GCTACCTCAA CTCGTCCTAC TTCGGTTTCC    1080
CAGACCCTAA GCTTTTCCCC TTTGCCAACA TCCTTACCAC AGATTTCCCC AGCTTCTTCT    1140
GCACTCTGGA CAACATCTGC CCTGTCAACA TCTCTGCCAG CTTCCGGCGA AAGCAGCCCC    1200
AGGAGGCAGC TGTTTGGCGA GTCCAGTCCC CCAAGCCCCT CTTTCGGACC CAGCTAAAGA    1260
CCCTGTTCCG TTCCTATTAC TCAGTGCAGA CAGCTGAGTG GCAGGCCCAT CCCCTCTATG    1320
GCTCCCGCCC CACGCTCCCG AGGTTTGCAC TCCATGACCA GCTCTTCTAC CTCAATGCCC    1380
TGGAGTGGGC GGCCAGCTCC GTGGAGGTGA TGGCCGTGGC TGCCAAGAAT GTGGCCTTGC    1440
TGGCTTACAA CCGCTGGTAC CAGGACCTAG ACAAGATTGA TCAAAAAGAT TTGATGCACA    1500
AGGTCAAGAC TGAACTGTGA GGGCTCTAGG GAGAGCCTGG GAACTTTCAT CCCCCACTGA    1560
AGATGGATCA TCCCACAGCA GCCCAGGACT GAATAAGCCA TGCTCGCCCA CCAGGCTTCT    1620
```

-continued

```
TTCTGACCCC TCATGTATCA AGCATCTCCA GGTGACCTAC TGTCTGCCTA TATTAAGGGT    1680

CCACACGGCG GCTGCTGCTT TTTTTTAAGG GGGAAAGTAA GAAAAGAGAA GGAAATCCAA    1740

GCCAGTATAT TTGTTTTATT TATTTTTTTT AAGAAGAAAA AAGTTCATCT TCACAAGGTG    1800

CTTCAGACTT GGTTTCTTAG CTAGAAACCA GAAGACTACG GGAGGGAATA TAAGGCAGAG    1860

AACTATGAGT CTTATTTTAT TACTGTTTTT CACTACCTAC TCCCACAATG GACAATCAAT    1920

TGAGGCAACC TACAAGAAAA CATTTACAAC CAGATGGTTA CAAATAAAGT AGAAGGGAAG    1980

ATCAGAAAAC CTAAGAAATG ATCATAGCTC CTGGTTACTG TGGACTTGAT GGATTTGAAG    2040

TACCTAGTTC AGAACTCCCT AGTCACCATC TCCAAGCCTG TCAACATCAC TGCATATTGG    2100

AGGAGATGAC TGTGGTAGGA CCCAAGGAAG AGATGTGTGC CTGAATAGTC GTCACCATAT    2160

CTCCAAGCTT CCTGGCAACC AGTGGGAAAA GAAACATGCG AGGCTGTAGG AAGAGGGAAG    2220

CTCTTCCTTG GCACCTAGAG GAATTAGCCA TTCTCTTCCT TATGCAAAGA TTGAGGAATG    2280

CAACAATATA AAGAAGAGAA GTCCCCAGAT GGTAGAGAGC AGTCATATCT TACCCCTAGA    2340

TGTTCATCCC AGCAGAAGAA AGAAGAAGGT GTTGGGGTAG GATTCTTCAG AGGTTAGCCT    2400

GGTACTTTCT CATCAGACAC TAGCTTGAAG TAAGAGGAGA ATTATGCTTT TCTTTGCTTT    2460

TTCTACAAAC CCTTAAAAAT CACTTGTTTT AAAAAGAAAG TAAAAGCCCT TTTCATTCAA    2520

AAAAAAAAAA AAAAAAAAA AAAAAAAAA AAAAAAAAA AAAAAA                     2567
```

SEQUENCES OF P56, PROTEINS WHICH AFFECT K-ATP CHANNELS

CROSS-REFERENCE TO RELATED APPLICATIONS

This application claims the benefit of US provisional application Serial No. 60/034,560 filed Dec. 30, 1996, under 35 USC §119(e)(i).

FIELD OF THE INVENTION

This invention relates to potassium channels and the p56 protein.

INFORMATION DISCLOSURE

The disclosures appearing in PCT/US95/14124, published May 30, 1996 as WO 96/16088, particularly page 1, is hereby incorporated by reference. Additional documents in the Detailed Description of the invention should be considered as part of the Information Disclosure.

BACKGROUND

The background appearing in PCT/US95/14124, published May 30, 1996 as WO 96/16088, particularly pages 1–5, are hereby incorporated by reference.

The isolation and identification of p56, a protein useful for the identification of selective drugs that will selectively open or close K channels was described in PCT/US95/14124, published May 30, 1996 as WO 96/16088. Herein the full length amino acid sequence of p56 and the nucleic acid sequence that code for p56 are described. Also described are the amino acid sequences and coding DNA that code for p56-2, a different p56 protein..

SUMMARY OF THE INVENTION

This invention describes the full length sequence of human p56 protein (p56-1), SEQ. ID. NO. 1 a related homolog (p56-2) SEQ. ID. NO. 3 and the nucleic acids that code for these proteins SEQ. ID. NOS. 2 and 4. The sequences are provided in Charts 1, 2, 3, and 4 and the sequence listings of the application SEQ. ID. NOS. 1–4. There are two unique p56 DNA sequences and proteins disclosed in this document. For the first p56 sequence, p56-1, the protein's entire amino acid sequence of p56 is provided in Chart 1 SEQ. ID. NO. 1 and the DNA coding for p56 is provided in Chart 2 SEQ. ID. NO. 2. For the second sequence, p56-2, the DNA and amino acids are disclosed Charts 3 SEQ. ID. NO. 3 and 4 SEQ. ID. NO. 4. Equivalents and obvious homologues are disclosed. Also disclosed by reference to PCT/US95/14124, published May 30, 1996 as WO 96/16088, hereby incorporated by reference, are cloning and other useful vectors for the sequence.

ADDITIONAL DESCRIPTION OF THE INVENTION AND DESCRIPTION OF THE PREFERRED EMBODIMENTS

The entire document numbered PCT/US95/14124, published May 30, 1996 as WO 96/16088, particularly pages 6–11 are hereby incorporated by reference.

UTILITY OF THE INVENTION

The utility of this invention is disclosed and supported by the disclosure appearing in PCT/US95/14124, published May 30, 1996 as WO 96/16088, particularly ages 11–12 are hereby incorporated by reference.

DETAILED DESCRIPTION OF THE INVENTION

A detailed description of the invention may be found by reference to PCT/US95/14124, published May 30, 1996 as WO 96/16088, particularly page 12, lines 33–35—page 20, hereby incorporated by reference. In addition to the PCT/WO publication the following additional remarks and materials disclose this invention.

Type I ATP-sensitive K channels ($I_{K-ATP}$) were first described in cardiac muscle (1) and have subsequently been characterized in skeletal muscle (2) vascular smooth muscle (3) and the β-cell of the pancreas (4-6). These type I channels are inhibited by micomolar concentrations of intracellular ATP and are insensitive to voltage and $Ca^{2+}$ (7). The β-cell $I_{K-ATP}$ channel is the most well understood in functional terms and it serves as a metabolic sensor that controls the release of insulin. Glucose stimulation of the β-cell results in an increase in the intracellular ATP/ADP ratio via glycolysis and the increase in ATP inhibits channel conductance. Because $I_{K-ATP}$ channels dominate the resting membrane potential of the β cell, inhibition of channel conductance results in a depolarization that activates voltage-dependent $Ca^{2+}$ channels and the resultant increase in intracellular $Ca^{2+}$ triggers insulin release. Pharmacological agents like sulfonylureas [$I_{K-ATP}$ blocker] or diazoxide [$I_{K-ATP}$ opener] stimulate or inhibit insulin release, respectively (8). In cardiac and skeletal muscle, the $I_{K-ATP}$ channels serve a similar function, coupling cell metabolism and electrical activity. These channels have a low open probability under resting conditions and are activated by a decline in the intracellular ATP/ADP ratio in response to either ischemic injury and/or exercise (2,9).

$I_{K-ATP}$ channels are unique among potassium channels because their activity can be regulated by a wide variety of structurally diverse pharmacological agents (10–15). These include both channel blockers (eg. sulfonylureas, guanidines and cyanoguanidines) and channel openers (eg. diazoxide, pinacidil, chromakalim, and minoxidil sulfate). This rich pharmacology translates into many opportunities for therapeutic intervention such as antidiabetics (sulfonylureas blockers), diuretics (guanidine and cyanoguanidine blockers), antihypertensives (openers like pinacidil and minoxidil sulfate) and agents that promote hair growth (minoxidil sulfate). Given the structural diversity among the chemical classes of agents that modify the activity of $I_{K-ATP}$ channels in various cell types, it is likely that the structure of these channels are complex. This diversity, coupled to the key role that $I_{K-ATP}$ channels play in linking cell excitability to metabolism, offers the hope that tissue selective modulators of $I_{K-ATP}$ channel activity can provide additional opportunities for the management of human disease.

Elucidation of the minimal structural components necessary to form functional $I_{K-ATP}$ channels was the result of two divergent efforts, namely the cloning and charaterization of either inward rectifier potassium channels or the high affinity sulfonylurea receptor (16,17). The first two members of the inward rectifier potassium channel gene family were isolated using expression cloning paradigms (18,19) and to date, homology cloning efforts have defined a total of 13 distinct genes in this class. Heterologous expression of the inward rectifier referred to as $K_{ir}$ 6.1 in human embryonic kidney cells led to the synthesis of a channel that displayed some of the properties of native $I_{K-ATP}$ channels (16). Subsequent cloning studies have defined a second member of the $K_{ir}$ 6 family, referred to as $K_{ir}$ 6.2 (19, 21–22). Molecular identification of the high affinity sulfonylurea receptor was facilitated by the use of sulfonylurea photoprobes to 'tag' the polypeptide responsible for high affinity sulfonylurea binding. Using either [$^3$H]-glyburide (23–25), [$^{125}$I]-glyburide analogs (26–28), or [$^{125}$I]/azido analogs of glyburide (29, 30), multiple investigators groups have identified a high affinity 140–150 kDa sulfonylurea binding protein in both β cells and in brain. Purification of photolabeled 140 kDa sulfonylurea receptor from β-cell lines followed by protein microsequence analysis and cDNA cloning has resulted in the molecular definition of the high affinity sulfonylurea receptor [SUR-1] (17). Subsequent cloning efforts have resulted in the identification of a paralog of SUR-1 referred to as SUR-2 (31–33). The primary structure of SUR-1 and SUR-2 resembles ABC cassette transporter proteins and heterologous expression of either SUR-1 or SUR-2 does not led to the synthesis of functional $I_{K-ATP}$ channels. Alternatively, co-expression of $K_{ir}$ 6.1/SUR-2 or $K_{ir}$ 6.2/SUR-1 combinations leads to the reconstitution of functional $I_{K-ATP}$ channels that display many of the electrophysiological and pharmacological signatures of native $I_{K-ATP}$ channels (31–33).

A parallel strategy for the identification of cyanoguanidine binding proteins was initiated with the synthesis and characterization of the azido photoprobe [$^3$H]-probe 1. Because the value of this photoprobe was reduced by its relatively low specific activity, a second generation cyanoguanidine analog, [$^{125}$I]-probe 2 was prepared and characterized. Photolabeling of intact rat aortic smooth muscle cells (A10) with $^{125}$I-probe 2, identified both high affinity (p56) and a low affinity (p47) binding sites that were displaced by homologous competition. Purification of $^{125}$I-p56 from A10 cells and protein microsequence analysis identified a unique twelve amino acid residue sequence tag derived from the NH$_2$ terminus of $^{125}$I-p56 and this identification was substantiated by the preparation and characterization of an antipeptide antibody that recognizes this sequence tag. This amino acid sequence tag was used to query expressed sequence tag (EST) databases to identify EST clones that potentially encode the human ortholog of the p56 sequence. Complete sequence analysis of multiple EST clones revealed a full-length cDNA that encoded the human ortholog of rat p56. Subsequent queries of an EST database with the full-length sequence of human p56 and sequence analysis revealed a second full-length human cDNA p56 paralog, referred to as p56-2 SEQ. ID. NO. 4. Human p56-1 SEQ. ID. NO. 2 and p56-2 SEQ. ID. NO. 4 were characterized by determining their tissue distribution of expression, their glycosylation in vitro and their ability to reconstitute the $^{125}$I-probe 2 binding site following transient expression in COS cells.

References by number above are reported here, all are incorporated by reference.

1. Noma, A. "ATP-regulated K$^+$ channels in cardiac muscle" *Nature* 305: 147–148 (1983).
2. Spruce, A. E., Standen, N. B. and Standfield, P. R. "Voltage-dependent ATP-sensitive potassium channels of skeletal muscle membrane" *Nature* 316: 736–738 (1985).
3. Standen, N. B., Quayle, J. M., Davies, N. W., Brayden, J. E., Huang, Y. and Nelson, M. T. "Hyperpolarizing vasodialators activate ATP-sensitive K$^+$ channels in arterial smooth muscle" *Science* 245: 177–180 (1989).
4. Cook, D. L. and Hales, C. N. "Intracellular ATP directly blocks K$^+$ channels in pancreatic beta cells" *Nature* 311: 271–273 (1984).
5. Sturgess, N. C., Ashford, M. L., Cook, D. L., and Hales, C. N. "The sulfonylurea receptor may be an ATP-sensitive potassium channel" *Lancet* 1:474–475 (1985).
6. Rorsman, P. and Trube, G. "Glucose-dependent K$^+$ channels in pancreatic beta cells are regulated by intracellular ATP" *Pflugers Arch* 405: 305–309 (1985).
7. Ashcroft, S. J. H. and Ashcroft F. M. "Properties and function of ATP-sensitive K$^+$ channels" *Cell Signal* 2:197–214 (1990).
8. Trube, G., Rorsman, P. and Ohno-Shosaku, T. "Opposite effects of tolbutamide and diazoxide on the ATP-dependent K$^+$ channel in mouse pancreatic β-cells" *Pflugers Arch* 407:493–499 (1986).
9. Escande, D. and Cavero, I. "K$^+$ channel openers and 'natural' cardioprotection" *Trends Pharmacol. Sci.* 13:269–271 (1992).
10. Gopalakrishnan, M., Janis, R. A. and Triggle, D. J. "ATP-sensitive K$^+$ channels: Pharmacologic properties, regulation and therapeutic potential" *Drug Dev. Res.* 28: 95–127 (1993).
11. Atwal, K. S. "Advances in the structure-activity relationships, mechanisms of action, and therapeutic utilities of ATP-sensitive potassium channel openers" *Drug Dev. Res.* 33:250–262 (1994).
12. Edwards, G. and Weston, A. H. "The pharmacology of ATP-sensitive potassium channels" *Ann.Rev. Pharmacol. Toxicol.* 33: 597–637 (1993).
13. de Weille, J. R. "Modulation of ATP sensitive potassium channels" *Cardiovascular Res.* 26: 1017–1020 (1992).
14. Atwal, K. S. "Modulation of potassium channels by organic molecules" *Medicinal Research Rev.* 12:569–591 (1992).
15. Robertson, D. W. and Steinberg, M. I. "Potassium channel modulators: Scientific applications and therapeutic promise" *J. Med. Chem.* 33: 1530–1541 (1990).
16. Inagaki, N., Tsuura, Y., Namba, N., Masuda, K, Gonoi, T., Horie, M., Seino, Y., Mizuta, M. and Seino, S. "Cloning and functional characterization of a novel ATP-sensitive potassium channel ubiquitously expressed in rat tissues, including pancreatic islets, pituitary, skeletal muscle and heart" *J. Biol. Chem.* 270: 5691–5694 (1995).
17. Aguilar-Bryan, L., Nichols, C. G., Wechsler, S. W., Clement, J. P., Boyd, A. E., Gonzalez, G., Herrera-Sosa, H., Nguy, K, Bryan, J. and Nelson, D. A. "Cloning of the β-cell high affinity sulfonylurea receptor; a regulator of insulin secretion" *Science* 268:423426 (1995).
18. Ho, K, Nichols, C. G., Lederer, W. J., Lytton, J., Vassilev, P. S, Kanazirska, M. V., and Hebert, S. C. "Cloning and expression of an inwardly rectifying ATP-regulated potassium channel" *Nature* 362:31–38 (1993).
19. Dascal, N., Schreibmayer, W., Lim, N. F., Wang, W., Chavkin, C., DiMagno, L., Labarca, C., Kieffer, B. L., Gaveriaux-Ruff, C., Trollinger, D., Lester, H. A., and Davidson, N. "Atrial G-protein activated K$^+$ channel: Expression cloning and molecular properties" *Proc. Natl. Acad. Sci. USA* 90:10235–10239 (1993).
21. Inagaki, N., Gonoi, T., Clement, J. P., Namba, N., Inazawa, J., Gonzalez, G., Aguilar-Bryan, L., Seino, S. and Bryan, J. "Reconstitution of $I_{K-ATP}$: an inward rectifier subunit plus the sulfonylurea receptor" *Science* 270: 1166–170 (1995).
22. Tokuyama, Y., Fan, Z., Furuta, H., Makielski, J. C., Polonsky, K. S., Bell, G. I. and Yano, H. "Rat inwardly rectifying potassium channel Kir 6.2: Cloning, electrophysiological characterization, and decreased expression in pancreatic islets of male Zucker diabetic fatty rats" *Biochem. Biophys. Res. Comm.* 220: 532–538 (1996).
23. Kramer, W., Oekonomopulos, R., Punter, J., and Summ, H. D. "Direct photolabeling of the putative sulfonylurea receptor in rat β-cell tumor membranes by [$^3$H]- glybenclamide" *FEBS Let* 229:355–359 (1988).

24. Bernardi, H., Fosset, M., and Lazdunski, M. "Characterization, purification and affinity labeling of the brain [$^3$H]-glybenclamide-binding protein, a putative neuronal ATP-regulated K$^+$ channel" *Proc. Natl. Acad. Sci. USA* 85:9816–9820 (1988).
25. Benardi, H., Fosset, M., and Lazdunski, M. "ATP/ADP Binding sites are present in the sulfonylurea binding protein associated with brain ATP-sensitive K$^+$ channels" *Biochemistry* 31:6328–6332 (1992).
26. Aguilar-Bryan, L., Nelson, D. A., Vu, Q., Humphrey, M. B., and Boyd III, A. E. "Photoaffinity labeling and partial purification of the β-cell sulfonylurea receptor using a novel, biologically active glyburide analog" *J. Biol. Chem.* 265:8218–8224 (1990).
27. Nelson, D.A., Aguilar-Bryan, L., and Bryan, J. "Specficity of photolabeling of β-cell membrane proteins with an $^{125}$I-labeled glyburide analog" *J. Biol. Chem.* 267:14928–14933 (1992).
28. Bernardi, H., De Weille, J. R, Epelbaum, J., Mourre, C., Amoroso, S., Slama, A., Fosset, M., and Lazdunski, M. "ATP-modulated K$^+$ channels sensitive to antidiabetic sulfonylureas are present in adenohypophysis and are involved in growth hormone release" *Proc. Natl. Acad. Sci. USA* 90:1340–1344 (1993).
29. Schwanstecher, M., Loser, S., Chudziak, F., and Panten, U. "Identification of a 38 kDa high affinity sulfonylurea-binding peptide in insulin-secreting cells and cerebral cortex" *J. Biol. Chem.* 269:17768–17771 (1994).
30. Schwanstecher, M., Loser, S., Chudziak, F., Bachmann, C., and Panten, U. "Photoaffinity labeling of cerebral sulfonylurea receptor using a novel radioiodinated azidoglibenclamide analogue" *J. Neurochem.* 63:698–708 (1994).
31. Inagaki, N., Gonoi, T., Clement, J. P., Wang, C.-Z., Aguilar-Bryan, L., Bryan, J. and Seino, S. "A family of sulfonylurea receptors determines the pharmacological properties of ATP-sensitive K$^+$ channels" *Neuron* 16: 1011–1017 (1996).
32. Chutkow, W. A., Simon, M. C., Le Beau, M. M. and Burant, C. F. "Cloning, tissue expression and chromosomal localization of SUR2, the putative drug-binding subunit of cardiac, skeletal muscle and vascular K$_{ATP}$ channels" *Diabetes* 45: 1439–1445 (1996).
33. Isomoto, S., Kondo, C., Yamada, M., Matsumoto, S., Higashiguchi, O., Horio, Y., Matsuzawa, Y. and Kurachi, Y. "A novel sulfonylurea receptor forms with BIR (K$_{ir}$ 6.2) a smooth muscle type ATP-sensitive K$^+$ channel" *J. Biol. Chem.* 271:24321–24324 (1996).

The NH2-terminal amino acid sequence was established, by the method described above in PCT/US95/14124, then various data bases and DNA libraries were repeatedly searched with no positive result. Finally, after numerous searches, the p56-1 NH2-terminal amino acid sequence (EPRAPPEKIAIGAG), disclosed in PCTIUS95/14124, published 30 May 1996 as WO 96/16088, led to the discovery of a human expressed sequence tag (EST) that displayed a significant match to the sequence disclosed in that PCT publication. A clone containing this sequence, identified as number 56-1, was obtained by searching various data bases and DNA libraries and the complete DNA sequence was determined.

Clone 56-1 contained a 1515 bp open-reading frame that encoded a 505 amino acid polypeptide with a predicted Mr for the mature protein of 52 kDa, close to the expected p56. The predicted sequence contained a signal peptide followed by a mature NH2-terminus that showed 11/14 exact matches with the rat p56 NH2-terminal sequence disclosed in PCT/US95/14124, published 30 May 1996 as WO 96/16088.

Consistent with biochemical data for rat p56, which demonstrated that p56 is a glycoprotein, the predicted polypeptide for clone 56-1 SEQ. ID. NO. 2 also contained 3 canonical acceptor sites for Asn-linked glycosylation. The predicted amino acid sequence has no significant homology to known sequences.

The predicted amino acid from clone 56-1 SEQ. ID. NO. 2 was analyzed using a variety of secondary structure prediction algorithms. A Rossman fold was detected near the NH2-terminus, indicating that this protein was likely to bind nucleotides like ATP. In contrast to the biochemical data on rat p56, no predicted transmembrane segments were detected but an endoplasmic reticulum retention signal (KEL-versus-the canonical KDEL) near the COOH-terminus was scored. A β-turn-β membrane association motif, similar to the P (pore)-region of voltage-gated-K$^+$-channels, was also detected. It appears that this polypeptide may associate with other K-channel pore-forming polypeptides (e.g. Kir 6.1 or 6.2) and regulate K channel activity. See, Inagaki, N., Tsuura, Y., Namba, N., Masuda, K., Gonoi, T., Horie, M., Seino, Y., Mizuta, M. and Seino, S. "Cloning and functional characterization of a novel ATP-sensitive potassium channel ubiquitously expressed in rat tissues, including pancreatic islets, pituitary, skeletal muscle and heart" *J. Biol. Chem.* 270: 5691–5694 (1995). AND. Inagaki, N., Gonoi, T., Clement, J. P., Namba, N., Inazawa, J., Gonzalez, G., Aguilar- Bryan, L., Seino, S. and Bryan, J. "Reconstitution of I$_{K-ATP}$: an inward rectifier subunit plus the sulfonylurea receptor" *Science* 270: 1166–170 (1995). Both articles incorporated by reference, and in particular aspects describing functional channel systems.

Using the sequence information disclosed herein one ordinarily skilled in the art should be able to use known PCT techniques to create, fashion, or produce clones having and or expressing the desired sequences described herein. The sequences can also be used in screens and assays for the detection of biologically active compounds. Additional descriptions of, procedures for and examples of these types of vectors, plasmids, cells, screens and assays can be found in case 6001. NCP, Ser. No. 08/709,923 filed Sep. 9, 1996, hereby incorporated by reference. In particular page 16 relating to procedures for preparing and using clones in assays especially relevant and incorporated by reference. In a similar manner additional descriptions of, procedures for and examples of these types of vectors, plasmids, cells, screens and assays can be found in WO 94/19464, PCT/US94/01210, published Sep. 1, 1994, hereby incorporated by reference. In particular, the pages relating to procedures for preparing and using clones in assays is especially relevant and incorporated by reference.

The second p56 sequence SEQ. ID. NOS. 3 and 4 was discovered according to the following procedures. Various data bases were queried with the amino acid sequence of human p56 using the FASTA search tool. In addition to identifying the known EST matches to p56, three additional ESTs that shared approximately 38–48% identity with p56 were also scored [447210, 2607571 and 2663551]. Alignment of the 5' EST sequence reads for these 3 clones with the p56 sequence showed that it was unlikely that the EST sequences overlapped and that clone 2607571 was most likely to be full-length. These clones were obtained and clone 2607571 was completely sequenced. This clone contained a 2.6 kb insert complete with a 1482 bp open reading frame that showed 41% shared identity with human p56. Motifs that were common to both predicted amino acid sequences include (1) a signal sequence, (2) Rossman fold, (3) canonical acceptor sites for Asn-linked glycosylation [3 in p56-1 and 6 in p56-2] and (4) an ER retention signal at the COOH-terminus [KTEL].

Comparison of the biochemical properties of p56-1

Biochemical characterization of $^{125}$I-p56-1 from A10 cells revealed a Triton X-100 soluble 56 kDa glycoprotein that could be de-glycosylated with N-glycanase to yield a 52 kDa form. These data are consistent with the $M_r$ of human p56-1 predicted from the cDNA sequence and the presence of canonical acceptor sites for Asn-linked glycosylation in the sequence. To establish these biochemical parameters experimentally for p56-1 SEQ. ID. NO. 2 and to investigate the glycosylation pattern of p56-2 SEQ. ID. NO. 4, both polypeptides were prepared by in vitro translation. Each expression plasmid was linearized by digestion with NotI and capped cRNA synthesized using T7-RNA polymerase. These cRNAs were then used to direct the synthesis of $^{35}$S-methionine labeled protein using rabbit reticulocyte lysates±canine pancreatic microsomes. The radiolabeled proteins were fractionated by SDS-PAGE and visualized by fluorography of the dried gel. P56-1 and p56-2 SEQ. ID. NOS. 2 and 4 have unglycosylated $M_r$ values of 52 kDa and 50 kDa, respectively. In the presence of canine pancreatic microsomes, multiple bands with higher $M_r$ values, including 56kDa, were also detected, indicating the addition of Asn-linked oligosaccharides to p56-1 SEQ. ID. NO. 2. In contrast to p56-1 SEQ. ID. NO. 2, p56-2 SEQ. ID. NO. 4 did not appear to be glycosylated under these conditions.

Tissue distribution of expression of human p56-1 and p56-2 SEQ. ID. NOS. 2 and 4

Comparison of Northern analysis and transcript imaging-The expression pattern of p56-1 and p56-2 SEQ. ID. NO. 4 transcripts was determined using both classical Northern blot analysis and by BLAST searching of EST database. For Northern blot analysis, poly A$^+$ RNAs isolated from various peripheral tissues and various brain regions were fractionated by electrophoresis under denaturing conditions and displayed on a nylon membrane. The blots were then visualized by hybridization to $^{32}$P-labeled coding sequence DNA probes prepared from either human p56-1 or human p56-2 SEQ. ID. NOS. 2 and 4. The p56-1 probe visualized a 6.0 kb transcript that was expressed at the highest level in skeletal muscle and lower levels detected in heart and pancreas. Minor signal was also detected in brain, placenta and liver while no transcript was detected in either lung or kidney under these conditions. Alternatively, BLAST searching revealed 20 ESTs derived from 11 different tissues matching the query with the complete p56-1 DNA sequence. These included the following ESTs; 5 from breast (4 normal/1 tumor), 3 from prostate (1 normal/2 tumor), 2 from brain, 2 from colon tumors, 2 from kidney and single ESTs from stomach, uterus, pituitary, nasal polyp, thyroid and mononuclear cells.

The human p56-2 probe visualized a 2.8 kb transcript that was expressed at the highest level in heart, brain, pancreas and placenta. No signal for p56-2 SEQ. ID. NO. 4 was observed in lung, liver, skeletal muscle or kidney under these conditions. p56-2 SEQ. ID. NO. 4 transcripts were widely expressed in brain regions, with the highest levels in the amygdala and lower levels in the hippocampus, the caudate nucleus, the corpus callosum, the substantia nigra and the subthalamic nucleus. Twenty ESTs matched the p56-2 query sequence and these were derived from 13 different tissues including 3 from pancreas, 3 from lung tumors, 2 from synovial membrane, 2 from leukocytes, 2 from hippocampus and single EST matches from heart, kidney, bladder, small intestine, adrenal, breast, prostate and nasal polyp.

Reconstitution of p56 photolabeling by transient expression of human p56-1 and p56-2 SEQ. ID. NOS. 2 and 4

Photolabeling of p56-1 SEQ. ID. NO. 2 with a cyanoguanidine opener photoprobe was reconstituted by transient heterologous expression of the p56-1 cDNA SEQ. ID. NO. 2 in COS7 cells. The coding sequence of human p56-1 SEQ. ID. NO. 2 was placed under the control of the SV40 immediate early promotor in the vector pSVL. This construct was introduced into COS7 cells using cationic liposomes and 48 hr post-infection, the transfected cells were photolabeled with $^{125}$I. Wild-type COS7 cells showed minimal photolabeling of a 52 kDa band and no p56. Alternatively, transient expression of human p56-1 in these same cells led to photolabeling of a polypeptide that migrated with a $M_r$ of 56 kDa.

CHARTS

The following charts disclose the full length human p56-1 and p56-2 SEQ. ID. NOS. 1 and 2 proteins and the DNA that code for those proteins. Chart 1 provides the sequences for the full length of the p56-1 protein SEQ. ID. NO. 1. The sequences in Chart 1 include the signal or leader sequence. The sequences in Chart 1 are also in sequence listing no. 1 SEQ. ID. NO. 1. Chart 2 provides the cDNA residues that code for the p56-1 protein SEQ. ID. NO. 2 and it includes untranslated sequences. All of the sequences in Chart 2 are provided for in sequence listing no. 2 SEQ. ID. NO. 2.

The p56-1 DNA SEQ. ID. NO. 2 sequence shown in Chart 2 contains one of many possible lengths of poly A tail, included as part of the cDNA sequence. This full-length cDNA contains: 1) a 5' untranslated sequence (alignment positions 1–39), 2) a coding sequence (alignment positions 40–1554), 3) a stop codon "TGA" (alignment position 1555–1557) and 4) a 3' untranslated sequence (alignment positions 1555–1724 with poly A). The coding sequence beginning with ATG at position 40 starts with a signal sequence that ends at position 123 while the mature sequence begins at position 124. These positions are noted on Charts 1 and 2 below.

The signal sequence or leader sequence is a hydrophobic region, usually about 20–25 amino acids, here 28 aa, at the N-terminus that 'signals' attachment of the ribosome to the endoplasmic reticulum and aids in the extrusion of the nacent polypeptide chain into the lumen of the ER. This signal sequence is cleaved off in the lumen by the signal peptidase. The untranslated sequences may have important regulatory functions such as governing MRNA stability and the like. The poly A track is added after transcription, the length is variable, often from 10–200 A's, here we show a 27 track poly A.

Charts 3 and 4 disclose the p56-2 proteins SEQ. ID. NO. 3 and the DNA that code for those proteins. Chart 3 provides the sequences for the full length of the p56-2 protein SEQ. ID. NO. 3. The sequences in Chart 3 include the signal or leader sequence. The sequences in Chart 3 are also in sequence listing no. 3 SEQ. ID. NO. 3. Chart 4 provides the cDNA residues that code for the p56-2 protein SEQ. ID. NO. 3 and it includes untranslated sequences. All of the sequences in Chart 4 are provided for in sequence listing no. 4 SEQ. ID. NO. 4.

The p56-2 DNA sequence SEQ. ID. NO. 4 shown in Chart 4 contains one of many possible lengths of poly A tail, included as part of the cDNA sequence. This fill-length cDNA contains: 1) a 5' untranslated sequence (alignment positions 1–35), 2) a coding sequence (alignment positions 36–1517), 3) a stop codon "TGA" (alignment position 1518–1520) and 4) a 3' untranslated sequence (alignment positions 1518–2567 with poly A). The coding sequence beginning with ATG at position 36 starts with a signal sequence. These positions are noted on Charts 3 and 4 below.

CHART 1

Amino acid sequence of the p56-1 protein SEQ. ID. NO. 1

```
  1 MGRVVAELVS SLLGLWLLLC SCGCPEGAEL RAPPDKIAII GAGIGGTSAA
                                              28↑↑29
 51 YYLRQKFGKD VKIDLFEREE VGGRLATMMV QGQEYEAGGS VIHPLNLHMK
101 RFVKDLGLSA VQASGGLLGI YNGETLVFEE SNWFIINVIK LVWRYGFQSL
151 RMHMWVEDVL DKFMRIYRYQ SHDYAFSSVE KLLHALGGDD FLGMLNRTLL
201 ETLQKAGFSE KFLNEMIAPV MRVNYGQSTD INAFVGAVSL SCSDSGLWAV
251 EGGNKLVCSG LLQASKSNLI SGSVMYIEEK TKTKYTGNPT KMYEVVYQIG
301 TETRSDFYDI VLVATPLNRK MSNITFLNFD PPIEEFHQYY QHIVTTLVKG
351 ELNTSIFSSR PIDKFGLNTV LTTDNSDLFI NSIGIVPSVR EKEDPEPSTD
401 GTYVWKIFSQ ETLTKAQILK LFLSYDYAVK KPWLAYPHYK PPEKCPSIIL
451 HDRLYYLNGI ECAASAMEMS AIAAHNAALL AYHRWNGHTD MIDQDGLYEK
```

CHART 2

Nucleotide sequence of the coding region for the p56-1 protein SEQ. ID. NO. 2.

```
   1 CGCTCGGAAT TCGGCTCGAG TGCAGAGCTT GTGGAGGCCA TGGGGCGCGT
                                               39↑↑40
  51 CGTCGCGGAG CTCGTCTCCT CGCTGCTGGG GTTGTGGCTG TTGCTGTGCA
 101 GCTGCGGATG CCCCGAGGGC GCCGAGCTGC GTGCTCCGCC AGATAAAATC
                  123↑↑124
 151 GCGATTATTG GAGCCGGAAT TGGTGGCACT TCAGCAGCCT ATTACCTGCG
 201 GCAGAAATTT GGGAAAGATG TGAAGATAGA CCTGTTTGAA AGAGAAGAGG
 251 TCGGGGCCG CCTGGCTACC ATGATGGTGC AGGGGCAAGA ATACGAGGCA
 301 GGAGGTTCTG TCATCCATCC TTTAAATCTG CACATGAAAC GTTTTGTCAA
 351 AGACCTGGGT CTCTCTGCTG TTCAGGCCTC TGGTGGCCTA CTGGGGATAT
 401 ATAATGGAGA GACTCTGGTA TTTGAGGAGA GCAACTGGTT CATAATTAAC
 451 GTGATTAAAT TAGTTTGGCG CTATGGATTT CAATCCCTCC GTATGCACAT
 501 GTGGGTAGAG GACGTGTTAG ACAAGTTCAT GAGGATCTAC CGCTACCAGT
 551 CTCATGACTA TGCCTTCAGT AGTGTCGAAA AATTACTTCA TGCTCTAGGA
 601 GGAGATGACT TCCTTGGAAT GCTTAATCGA ACACTTCTTG AAACCTTGCA
 651 AAAGGCCGGC TTTTCTGAGA AGTTCCTCAA TGAAATGATT GCTCCTGTTA
 701 TGAGGGTCAA TTATGGCCAA AGCACGGACA TCAATGCCTT TGTGGGGGCG
 751 GTGTCACTGT CCTGTTCTGA TTCTGGCCTT TGGGCAGTAG AAGGTGGCAA
 801 TAAACTTGTT TGCTCAGGGC TTCTGCAGGC ATCCAAAAGC AATCTTATAT
 851 CTGGCTCAGT AATGTACATC GAGGAGAAAA CAAAGACCAA GTACACAGGA
 901 AATCCAACAA AGATGTATGA AGTGGTCTAC CAAATTGGAA CTGAGACTCG
 951 TTCAGACTTC TATGACATCG TCTTGGTGGC CACTCCGTTG AATCGAAAAA
1001 TGTCGAATAT TACTTTTCTC AACTTTGATC CTCCAATTGA GGAATTCCAT
```

CHART 2-continued

Nucleotide sequence of the coding region for the p56-1 protein SEQ. ID. NO. 2.

```
1051 AAATATTATC AACATATAGT GACAACTTTA GTTAAGGGGG AATTGAATAC

1101 ATCTATCTTT AGCTCTAGAC CCATAGATAA ATTTGGCCTT AATACAGTTT

1151 TAACCACTGA TAATTCAGAT TTGTTCATTA ACAGTATTGG GATTGTGCCC

1201 TCTGTGAGAG AAAAGGAAGA TCCTGAGCCA TCAACAGATG AACATATGT

1251 TTGGAAGATC TTTTCCCAAG AAACTCTTAC TAAAGCACAA ATTTTAAAGC

1301 TCTTTCTGTC CTATGATTAT GCTGTGAAGA AGCCATGGCT TGCATATCCT

1351 CACTATAAGC CCCGGAGAA ATGCCCCTCT ATCATTCTCC ATGATCGACT

1401 TTATTACCTC AATGGCATAG AGTGTGCAGC AAGTGCCATG GAGATGAGTG

1451 CCATTGCAGC CCACAACGCT GCACTCCTTG CCTATCACCG CTGGAACGGG

1501 CACACAGACA TGATTGATCA GGATGGCTTA TATGAGAAAC TTAAAACTGA

1551 ACTATGAAGT GACACACTCC TTTTTCCCCT CCTAGTTCCA AATGACTATC
     1554↑↑↑1558
         stop
1601 AGTGGCAAAA AAGAACAAAA TCTGAGCAGA GATGATTTTG AACCAGATAT

1651 TTTGCCATTA TCATTGTTTA ATAAAAGTAA TCCCTGCTGG TCATAGGAAA

1701 AAAAAAAAAA AAAAAAAAA AAAA
```

Chart 3

Amino acid sequence of the p56-2 protein SEQ. ID. NO. 3.

```
  1 MARAAPLLAA LTALLAAAAA GCDAPPGKIA VVGAGIGGSA VAHFLQQHFG

51 PRVQIDVYEK GTVGGRLATI SVNKQHYESG AASFHSLSLH MQDFVKLLGL

101 RHRREVVGRS AIFGGEHFML EETDWYLLNL FRLWWHYGIS FLRLQMWVEE

151 VMEKFMRIYK YQAHGYAFSG VEELLYSLGE STFVNMTQHS VAESLLQVGV

201 TQRFIDDVVS AVLRASYGQS AAMPAFAGAM SLAGAQGSLW SVEGGNKLVC

251 SGLLKLTKAN VIHATVTSVT LHSTEGKALY QVAYENEVGN SSDFYDIVVI

301 ATPLHLDNSS SNLTFAGFHP PIDDVQGSFQ PTVVSLVHGY LNSSYFGFPD

351 PKLFPFANIL TTDFPSFFCT LDNICPVNIS ASFRRKQPQE AAVWRVQSPK

401 PLFRTQLKTL FRSYYSVQTA EWQAHPLYGS RPTLPRFALH DQLFYLNALE

451 WAASSVEVMA VAAKNVALLA YNRWYQDLDK IDQKDLMHKV KTEL
```

Chart 4

Nucleotide sequence of the coding region for the p56-2 protein SEQ. ID. NO. 4.

```
  1 CCTGAATCCG GCGTGCTGCC CGCTCGCCGC CCGCCATGGC CCGCGCAGCC
                                           35↑↑36
 51 CCGCTGCTCG CCGCGTTGAC CGCGCTCCTC GCCGCCGCCG CTGCTGGCGG

101 AGATGCCCCG CCGGGCAAAA TCGCGGTGGT TGGGGCTGGG ATTGGGGGCT

151 CTGCTGTGGC CCATTTTCTC CAGCAGCACT TTGGACCTCG GGTGCAGATC

201 GACGTGTACG AGAAGGGAAC CGTGGGTGGC CGCTTGGCCA CCATCTCAGT
```

```
 251 CAACAAGCAG CACTATGAGA GCGGGCTGC CTCCTTCCAC TCCCTGAGCC
 301 TGCACATGCA GGACTTCGTC AAGCTGCTGG GGCTGAGGCA CCGGCGCGAG
 351 GTGGTGGGCA GGAGCGCCAT CTTCGGCGGG GAGCACTTCA TGCTGGAGGA
 401 GACTGACTGG TACCTGCTGA ACCTCTTCCG CCTCTGGTGG CACTATGGCA
 451 TCAGCTTCCT GAGGCTGCAG ATGTGGGTGG AGGAGGTCAT GGAGAAGTTC
 501 ATGAGGATCT ATAAGTACCA GGCCCACGGC TATGCCTTCT CGGGTGTGGA
 551 GGAGCTGCTC TACTCACTGG GGGAGTCCAC CTTTGTTAAC ATGACCCAGC
 601 ACTCTGTGGC TGAGTCCCTG CTGCAGGTGG GCGTCACGCA GCGCTTTATT
 651 GATGATGTCG TTTCTGCTGT CCTGCGGGCC AGCTATGGCC AGTCAGCAGC
 701 GATGCCCGCC TTTGCAGGAG CCATGTCACT AGCCGGGGCC CAAGGCAGCC
 751 TGTGGTCTGT GGAAGGAGGC AATAAGCTGG TTTGTTCCGG TTTGCTGAAG
 801 CTCACCAAGG CCAATGTGAT CCATGCCACA GTGACCTCTG TGACCCTGCA
 851 CAGCACAGAG GGGAAAGCCC TGTACCAGGT GGCGTATGAG AATGAGGTAG
 901 GCAACAGCTC TGACTTCTAT GACATCGTGG TCATCGCCAC CCCCCTGCAC
 951 CTGGACAACA GCAGCAGCAA CTTAACCTTT GCAGGCTTCC ACCCGCCCAT
1001 TGATGACGTG CAGGGCTCTT CCAGCCCAC CGTCGTCTCC TTGGTCCACG
1051 GCTACCTCAA CTCGTCCTAC TTCGGTTTCC CAGACCCTAA GCTTTTCCCC
1101 TTTGCCAACA TCCTTACCAC AGATTTCCCC AGCTTCTTCT GCACTCTGGA
1151 CAACATCTGC CCTGTCAACA TCTCTGCCAG CTTCCGGCGA AAGCAGCCCC
1201 AGGAGGCAGC TGTTTGGCGA GTCCAGTCCC CCAAGCCCCT CTTTCGGACC
1251 CAGCTAAAGA CCCTGTTCCG TTCCTATTAC TCAGTGCAGA CAGCTGAGTG
1301 GCAGGCCCAT CCCCTCTATG GCTCCCGCCC CACGCTCCCG AGGTTTGCAC
1351 TCCATGACCA GCTCTTCTAC CTCAATGCCC TGGAGTGGGC GGCCAGCTCC
1401 GTGGAGGTGA TGGCCGTGGC TGCCAAGAAT GTGGCCTTGC TGGCTTACAA
1451 CCGCTGGTAC CAGGACCTAG ACAAGATTGA TCAAAAAGAT TTGATGCACA
1501 AGGTCAAGAC TGAACTGTGA GGGCTCTAGG GAGAGCCTGG GAACTTTCAT
                              1518↑↑  ↑↑↑1521
                                stop
1551 CCCCCACTGA AGATGGATCA TCCCACAGCA GCCCAGGACT GAATAAGCCA
1601 TGCTCGCCCA CCAGGCTTCT TTCTGACCCC TCATGTATCA AGCATCTCCA
1651 GGTGACCTAC TGTCTGCCTA TATTAAGGGT CCACACGGCG GCTGCTGCTT
1701 TTTTTTAAGG GGGAAAGTAA GAAAAGAGAA GGAAATCCAA GCCAGTATAT
1751 TTGTTTTATT TATTTTTTTT AAGAAGAAAA AAGTTCATCT TCACAAGGTG
1801 CTTCAGACTT GGTTTCTTAG CTAGAAACCA GAAGACTACG GGAGGGAATA
1851 TAAGGCAGAG AACTATGAGT CTTATTTTAT TACTGTTTTT CACTACCTAC
1901 TCCCACAATG GACAATCAAT TGAGGCAACC TACAAGAAAA CATTTACAAC
1951 CAGATGGTTA CAAATAAAGT AGAAGGGAAG ATCAGAAAAC CTAAGAAATG
2001 ATCATAGCTC CTGGTTACTG TGGACTTGAT GGATTTGAAG TACCTAGTTC
2051 AGAACTCCCT AGTCACCATC TCCAAGCCTG TCAACATCAC TGCATATTGG
2101 AGGAGATGAC TGTGGTAGGA CCCAAGGAAG AGATGTGTGC CTGAATAGTC
2151 GTCACCATAT CTCCAAGCTT CCTGGCAACC AGTGGGAAAA GAAACATGCG
2201 AGGCTGTAGG AAGAGGGAAG CTCTTCCTTG GCACCTAGAG GAATTAGCCA
2251 TTCTCTTCCT TATGCAAAGA TTGAGGAATG CAACAATATA AGAAGAGAA
```

```
2301 GTCCCCAGAT GGTAGAGAGC AGTCATATCT TACCCCTAGA TGTTCATCCC

2351 AGCAGAAGAA AGAAGAAGGT GTTGGGGTAG GATTCTTCAG AGGTTAGCCT

2401 GGTACTTTCT CATCAGACAC TAGCTTGAAG TAAGAGGAGA ATTATGCTTT

2451 TCTTTGCTTT TTCTACAAAC CCTTAAAAAT CACTTGTTTT AAAAAGAAAG

2501 TAAAAGCCCT TTTCATTCAA AAAAAAAAAA AAAAAAAAAA AAAAAAAAA

2551 AAAAAAAAAA AAAAAAA  2567
```

---

What is claimed is:

1. An isolated protein selected from the proteins comprising the proteins disclosed in SEQ. ID. NOS. 1 and 3.

2. An isolated protein of claim 1 comprising the protein disclosed in SEQ. ID. NO. 1.

3. An isolated protein of claim 1 comprising the protein disclosed in SEQ. ID. NO. 3.

4. A nucleic acid molecule encoding the proteins selected from the proteins comprising the proteins disclosed in SEQ. ID. NOS. 1 and 3, incorporated into a vector selected from a cloning vector, a shuttle vector or an expression vector, where the vectors are plasmids.

5. The plasmid of claim 4 adapted for expression in a bacterial cell, a mammalian cell, and a yeast cell.

* * * * *